United States Patent
Min et al.

(10) Patent No.: US 8,731,665 B1
(45) Date of Patent: May 20, 2014

(54) POSTURE DETECTION USING PRESSURE AND OTHER PHYSIOLOGIC SENSORS

(75) Inventors: Xiaoyi Min, Thousand Oaks, CA (US); Laleh Jalali, Moorpark, CA (US); Steve Koh, South Pasadena, CA (US); Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1177 days.

(21) Appl. No.: 11/923,286

(22) Filed: Oct. 24, 2007

(51) Int. Cl.
*A61N 1/00* (2006.01)

(52) U.S. Cl.
USPC .......................................................... 607/18

(58) Field of Classification Search
None
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,729,376 A | 3/1988 | DeCote, Jr. | |
| 4,969,467 A | 11/1990 | Callaghan et al. | |
| 5,330,507 A | 7/1994 | Schwartz | |
| 5,350,410 A | 9/1994 | Kleks et al. | |
| 5,383,473 A | 1/1995 | Moberg | |
| 5,458,626 A | 10/1995 | Krause | |
| 5,466,254 A | 11/1995 | Helland | |
| 5,593,431 A | 1/1997 | Sheldon | |
| 5,700,282 A | 12/1997 | Zabara | |
| 6,044,297 A * | 3/2000 | Sheldon et al. | 607/17 |
| 6,473,644 B1 | 10/2002 | Terry, Jr. et al. | |
| 6,625,493 B2 | 9/2003 | Kroll et al. | |
| 6,658,292 B2 | 12/2003 | Kroll et al. | |
| 6,662,047 B2 | 12/2003 | Sorensen et al. | |
| 6,937,896 B1 | 8/2005 | Kroll | |
| 6,937,900 B1 | 8/2005 | Pianca et al. | |
| 6,975,904 B1 * | 12/2005 | Sloman | 607/28 |
| 7,336,999 B1 * | 2/2008 | Koh | 607/27 |
| 7,373,204 B2 | 5/2008 | Gelfand et al. | |
| 7,636,599 B1 * | 12/2009 | Koh et al. | 607/17 |
| 2002/0147475 A1 | 10/2002 | Scheiner et al. | |
| 2002/0147476 A1 | 10/2002 | Daum | |
| 2003/0040778 A1 | 2/2003 | Kroll et al. | |
| 2003/0045909 A1 | 3/2003 | Gross et al. | |
| 2003/0045910 A1 | 3/2003 | Sorensen et al. | |
| 2003/0060857 A1 | 3/2003 | Perrson et al. | |
| 2005/0148897 A1 * | 7/2005 | Cho et al. | 600/533 |
| 2005/0288718 A1 | 12/2005 | Sunagawa et al. | |
| 2006/0025699 A1 | 2/2006 | Maile et al. | |
| 2006/0116721 A1 | 6/2006 | Yun et al. | |

FOREIGN PATENT DOCUMENTS

WO 03041559 A2 5/2003

OTHER PUBLICATIONS

NonFinal Office Action, mailed Dec. 29, 2006—Related U.S. Appl. No. 10/972,278.
NonFinal Office Action, mailed Jul. 9, 2007—Related U.S. Appl. No. 10/972,278.

(Continued)

*Primary Examiner* — Christopher D Koharski
*Assistant Examiner* — Elizabeth K So

(57) ABSTRACT

Systems and methods are provided for detecting the orientation and/or movement of a patient having an implantable cardiac stimulation device and evaluating whether a change in the patient's cardiac activity can be at least in part due to a change in the patient's orientation. In one particular embodiment, signals from an orientation sensor and/or a pressure sensor are evaluated to determine static positional orientation of the patient and determine based on the static orientation whether the patient's cardiac activity is abnormal.

15 Claims, 9 Drawing Sheets

(56) References Cited

OTHER PUBLICATIONS

Final Office Action, mailed Oct. 4, 2007—Related U.S. Appl. No. 10/972,278.
NonFinal Office Action, mailed Mar. 4, 2008—Related U.S. Appl. No. 10/972,278.
Final Office Action, mailed Nov. 17, 2008—Related U.S. Appl. No. 10/972,278.
Advisory Action, mailed Feb. 10, 2009—Related U.S. Appl. No. 10/972,278.
Restriction Requirement, mailed Aug. 25, 2009—Related U.S. Appl. No. 10/972,278.
NonFinal Office Action, mailed Mar. 17, 2010—Related U.S. Appl. No. 10/972,278.
Final Office Action, mailed Aug. 6, 2010—Related U.S. Appl. No. 10/972,278.

* cited by examiner

POSTURE DETECTION USING PRESSURE AND OTHER PHYSIOLOGIC SENSORS

BACKGROUND OF THE INVENTION

1. Field of the Invention

The invention relates to the field of implantable medical devices and to systems and methods of detecting the orientation of a patient having an implantable medical device.

2. Description of the Related Art

A variety of implantable medical devices are known to automatically monitor a patient's physiologic condition and to selectively provide therapy when needed. Pacemakers and/or cardioverter defibrillators (ICDs) are implantable medical devices which are configured to monitor a patient's cardiac activity and selectively provide therapy for a variety of cardiac arrhythmias. Cardiac arrhythmia can be defined as a group of conditions in which the muscle contraction of the heart is irregular, e.g., faster or slower than normal. Implantable pacemakers and/or ICDs typically include a stimulation pulse generator which generates therapeutic stimulation for delivery to patient tissue and a microprocessor-based controller which regulates the delivery of that therapy. Implantable pacemakers and/or ICDs are also typically configured to monitor the patient's cardiac activity, to detect any possible abnormalities or cardiac arrhythmias based on the monitored cardiac activity, and to respond accordingly when an abnormality is detected. For example, therapeutic stimulation may be provided when the implantable pacemaker and/or ICD detects a cardiac arrhythmia.

The cardiac signals that are monitored for detecting cardiac arrhythmias may also be useful in detecting other potential abnormalities that may be indicative of future heart problems. For example, a consistently low amplitude of the monitored cardiac signal may be indicative of a heart problem which can lead to future heart failure, if not detected early. Thus, the cardiac signals that are monitored can be stored and analyzed for early detection of other potential problems.

However, changes in the patient's cardiac activity are not always indicative of abnormalities or cardiac arrhythmias. Changes in the orientation of the patient, for example, can also result in changes in the monitored cardiac activity. Generally, abnormalities detected in the intracardiac electrogram (IEGM) signals that exceed predetermined thresholds may result in changes in the performance of the ICD. Thus, a change in the IEGM signal that is caused by factors other than heart abnormalities or cardiac arrhythmias, if not properly detected, may result in changes in the performance of the ICD and/or improper diagnosis of a heart problem. Further, the metabolic needs of the patient may vary depending upon the patient's posture. As such, being able to distinguish between various patient postures such as, patient lying down, lying on the right side, lying on the left side, sitting, or standing up can be helpful in providing input to the implanted device to ensure that the patient's heart is being stimulated appropriately based upon the patient's need.

Accordingly, there is a need for implantable pacemakers and/or ICDs to detect changes in the orientation of the patient and to properly relate any changes in the cardiac activity to changes in the orientation.

SUMMARY OF THE INVENTION

This need is satisfied by the invention which, in one embodiment, includes an implantable cardiac stimulation device for a patient comprising at least one lead adapted to be implanted within the patient so as to be able to provide electrical stimulation to the heart of the patient, at least one electrical sensor that senses the electrical activity of the heart of the patient, an orientation sensor that detects parameters of the patient that are indicative of the orientation of the patient, a controller that induces the lead to provide electrical stimulation to the heart of the patient wherein the controller receives signals from the electrical sensor and the orientation sensor, wherein the controller evaluates the signals from the electrical sensor to determine whether the signals are potentially indicative of possible abnormality in the patient's heart function and when the controller determines that the electrical signals are potentially indicative of possible abnormalities in the patient's heart function, the controller then evaluates the orientation sensor to determine whether the possible abnormalities are due, at least in part, to a change in the orientation of the patient.

In one embodiment, the controller is adapted to evaluate whether the possible abnormalities are due to a change in the orientation of the patient and the controller is configured to store the signals relating to the possible abnormality in a memory and set a flag in the memory for future follow up when the controller determines that the possible abnormalities are not due to a change in the patient's orientation.

In another embodiment, the controller is adapted to evaluate whether the possible abnormalities are due to a change in the orientation of the patient and the controller is configured to change the parameters of the electrical stimulation applied to the heart, when the controller determines that the possible abnormalities are not due to a change in the patient's orientation. In yet another embodiment, the lead is adapted to both provide electrical stimulation and detect electrical activity of the heart so that the lead comprises at least one electrical sensor.

In another embodiment, the electrical sensor senses an internal electrogram signal which includes signals indicative of intrinsic heart activity and evoked heart activity in response to the delivery of therapeutic electrical stimulations via at least one lead. In one embodiment, the amplitude of the internal electrogram signal changes as a result of a change in the patient's orientation. In another embodiment, the controller monitors the evoked heart activity to determine whether the evoked heart activity has an amplitude that is less than a pre-determined threshold and when the amplitude is less than a pre-determined threshold, the controller determines the signals to be potentially indicative of possible abnormalities. In some embodiments, the controller then determines using the orientation sensor whether the possible abnormality is an artifact of the patient's orientation.

In other embodiments, the orientation sensor comprises an accelerometer and the accelerometer is configured to detect the patient's static positional orientation. In some embodiments, the accelerometer is configured to detect the patient's movement. In other embodiments, the orientation sensor further comprises at least one pressure sensor that senses pressure within one or more of the heart chambers and the orientation signal of the patient is determined using both the pressure sensor and the accelerometer. In some embodiments, the pressure sensor is connected to the tip of the lead. In other embodiments, the pressure sensor is configured to sense pressure within the left atrium, the right atrium, or the right ventricle of the heart.

Another embodiment of the invention includes an implantable cardiac stimulation device for a patient comprising at least one lead adapted to be implanted within the patient so as to be able to provide electrical stimulation to the heart of the patient, at least one electrical sensor that senses the electrical activity of the heart of the patient, a pressure sensor that senses the pressure within at least one chamber of the heart, an orientation sensor that detects parameters of the patient that are indicative of the orientation of the patient, and a controller that induces the at least one lead to provide electrical stimulation to the heart of the patient wherein the controller receives signals from the at least one electrical sensor, the orientation sensor, and the pressure sensor and wherein the controller evaluates the signals from the at least one electrical sensor to determine whether the signals are potentially indicative of possible abnormality in the patient's heart function and when the controller determines that the electrical signals are potentially indicative of possible abnormalities in the patient's heart function, the controller then evaluates signals received from the pressure sensor and the orientation sensor to determine whether the possible abnormalities are due, at least in part, to a change in the orientation of the patient and uses the signals to adjust the electrical stimulation therapy being provided to the heart via the at least one lead.

In one embodiment, the orientation sensor in the implantable cardiac stimulation device comprises an accelerometer. In another embodiment, the lead is adapted to both provide electrical stimulation and to also detect electrical activity of the heat so that the lead comprises the electrical sensor.

In another embodiment, the controller in the implantable cardiac stimulation device evaluates the signals received from the pressure sensor and the orientation sensor to detect if the patient has stood up and evaluates the signals received from the pressure sensor to detect whether the patient suffers from orthostatic hypotension. In one embodiment, the controller is also configured to adjust parameters of the electrical stimulation applied to the heart, when the controller detects that the patient suffers from orthostatic hypotension and that the patient has stood up. In one embodiment, the parameters of the electrical stimulation comprise a pacing rate.

Yet another embodiment of the invention includes a method of controlling a cardiac rhythm management device, comprising receiving an actual evoked response signal in response to an electrical stimulus provided to a medical patient, determining an orientation of the patient by sensing a patient position, selecting an expected evoked response signal from a plurality of stored evoked response signals, wherein the selection is based at least in part on the orientation, and determining a patient therapy based at least in part upon a comparison of the actual evoked response signal to the selected expected evoked response signal.

In one embodiment, determining a patient therapy comprises setting a stimulation voltage amplitude of the cardiac rhythm management device. In another embodiment, determining a patient therapy comprises setting a stimulation voltage timing parameter of the cardiac rhythm management device.

Another embodiment of the invention includes an implantable cardiac stimulation device for a patient comprising at least one lead adapted to be implanted within the patient so as to be able to provide an electrical stimulus to the heart of the patient, at least one electrical sensor that senses an actual evoked response signal indicative of the electrical activity of the heart of the patient in response to the electrical stimulus, an orientation sensor that detects orientation parameters of the patient that are indicative of the orientation of the patient, a controller that induces the at least one lead to provide the electrical stimulus to the heart of the patient, wherein the controller receives the actual evoked response signal from the at least one electrical sensor and the orientation parameters from the orientation sensor, wherein the controller selects an expected evoked response signal from a plurality of stored evoked response signals based at least in part on the orientation parameters, and wherein the controller determines a patient therapy based at least in part upon a comparison of the actual evoked response signal to the selected expected evoked response signal.

In one embodiment, the patient therapy of the implantable cardiac stimulation device comprises a stimulation voltage amplitude of the implantable cardiac stimulation device. In another embodiment, the patient therapy comprises a stimulation voltage timing parameter of the implantable cardiac stimulation device.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
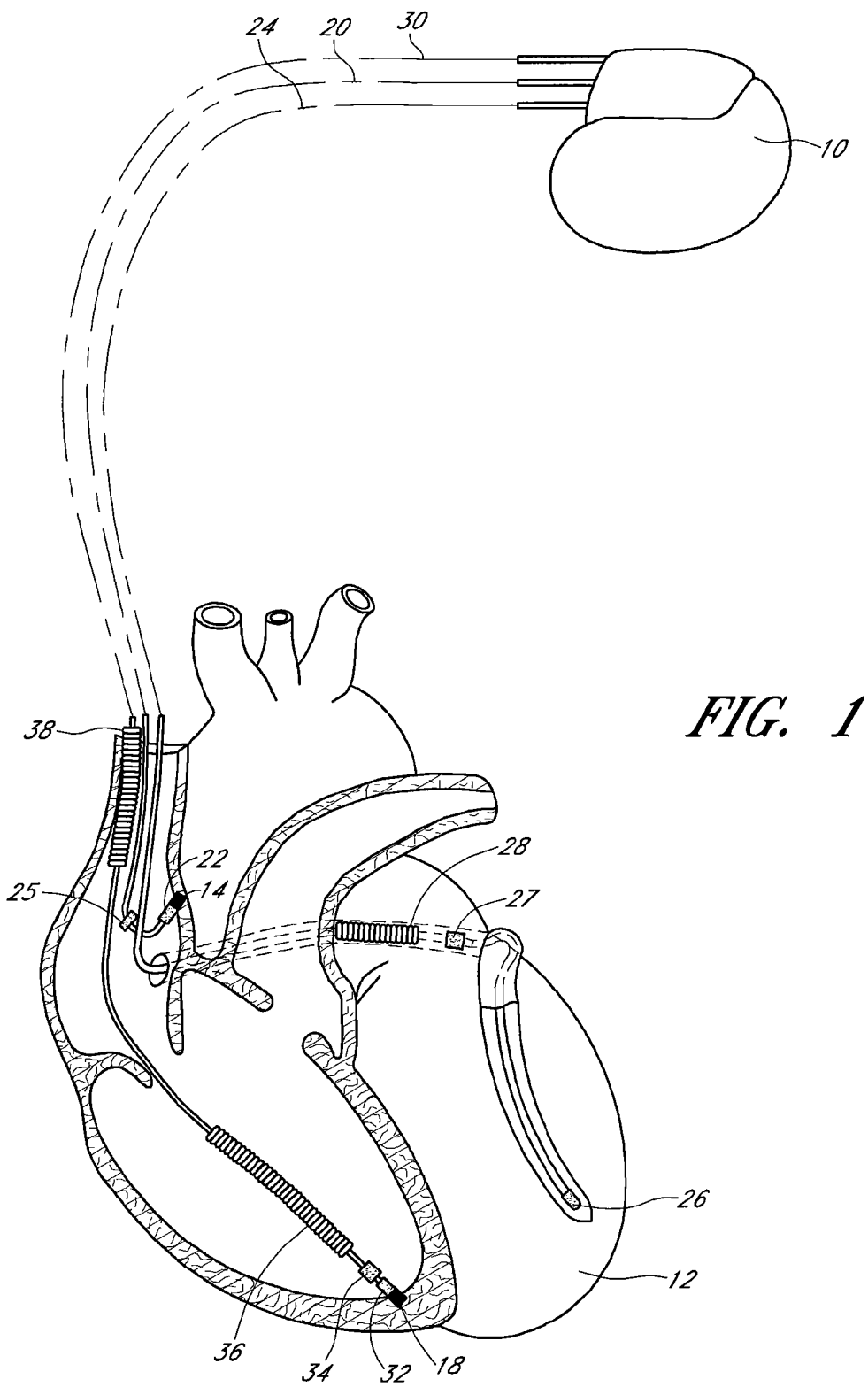
FIG. 1 is a simplified diagram illustrating a therapeutic appliance with an implantable stimulation device in electrical communication with at least three leads implanted into a patient's heart for delivering multi-chamber stimulation and shock therapy and a mechanical structural support to restrain excessive distension of the heart.

As shown in FIG. 1, there is a stimulation device 10 in electrical communication with a patient's heart 12 by way of three leads 20, 24 and 30, suitable for delivering multi-chamber stimulation and shock therapy. The stimulation device 10 is coupled to an implantable right atrial lead 20 which allows the device 10 to sense atrial cardiac and right atrial pressure signals, and to provide right atrial chamber stimulation therapy. The right atrial lead 20 has at least an atrial tip electrode 22, a right atrial ring electrode 25, and a right atrial pressure sensor 14. The atrial tip electrode 22, right atrial ring electrode 25, and right atrial pressure sensor 14 are typically implanted in the patient's right atrial appendage, as shown. In the illustrated embodiment, the right atrial pressure sensor 14 is disposed at the atrial tip electrode 22. In other embodiments, the right atrial pressure sensor 14 may be located at other locations in the right atrial appendage. For example, the right atrial pressure sensor 14 may be positioned near or in the superior vena cava (SVC) such as near the SVC coil electrode 38.

The stimulation device 10 is coupled to a coronary sinus lead 24, which is designed for placement in the coronary sinus region via the coronary sinus ostium (OS). The coronary sinus lead 24 works with the simulation device 10 to sense left atrial and ventricular cardiac signals, sense left atrial pressure signals, and provide left chamber pacing therapy. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals. Furthermore, the coronary sinus lead 24 is designed to receive left atrial pressure signals using a left atrial pressure sensor 15 (shown in FIG. 1A). Additionally, the coronary sinus lead 24 is configured to deliver left ventricular pacing therapy using at least a left ventricular tip electrode 26, deliver left atrial pacing therapy using at least a left atrial ring electrode 27, and/or deliver shocking therapy using at least a left atrial coil electrode 28. For a complete description of a coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which are hereby incorporated herein by reference.

Figure 1A:
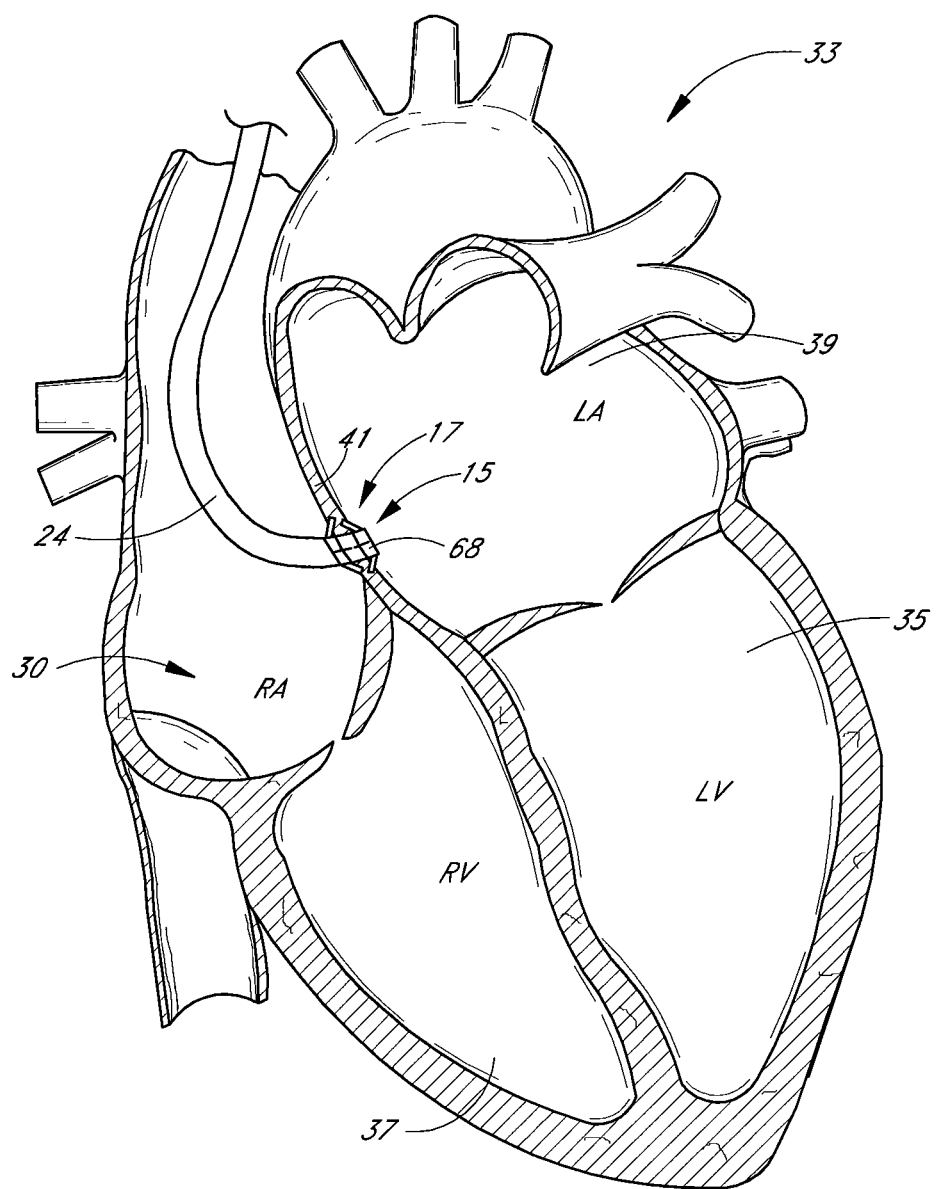
FIG. 1A is a simplified diagram illustrating one embodiment of a lead implanted into a patient's heart for sensing pressure in the left atrial chamber of the patient's heart.

As illustrated in FIG. 1A, the left atrial pressure sensor 15 is implanted percutaneously in the patient by approaching the left atrium 39 through the right atrium 30, penetrating the patient's atrial septum 41 and positioning the pressure sensor 15 in the atrial septum 41. Other configurations are also possible. For example, the pressure sensor 15 can also be positioned on the septal wall of the left atrium 39 or inside the patient's left atrium 39.

Referring back to FIG. 1, the stimulation device 10 is also in electrical communication with the patient's heart 12 by way of an implantable right ventricular lead 30. In one embodiment, the right ventricular lead 30 includes a right ventricular tip electrode 32 connected to a right ventricular pressure sensor 18, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex. This causes the RV coil electrode 36 to be positioned in the right ventricle and the SVC coil electrode 38 to be positioned in the superior vena cava.

Accordingly, the right ventricular lead 30 is capable of receiving cardiac signals and pressure signals, and delivering stimulation in the form of pacing and shock therapy to the right ventricle. In this embodiment, the right ventricular pressure sensor 18 is connected to the right ventricular tip electrode 32. In other embodiments, the right ventricular pressure sensor 18 may be disposed at other locations along the right ventricular lead 30. For example, the right ventricular pressure sensor 18 may be disposed near the end of the lead 30 or it may be disposed near the coil electrode 36.

Figure 2:
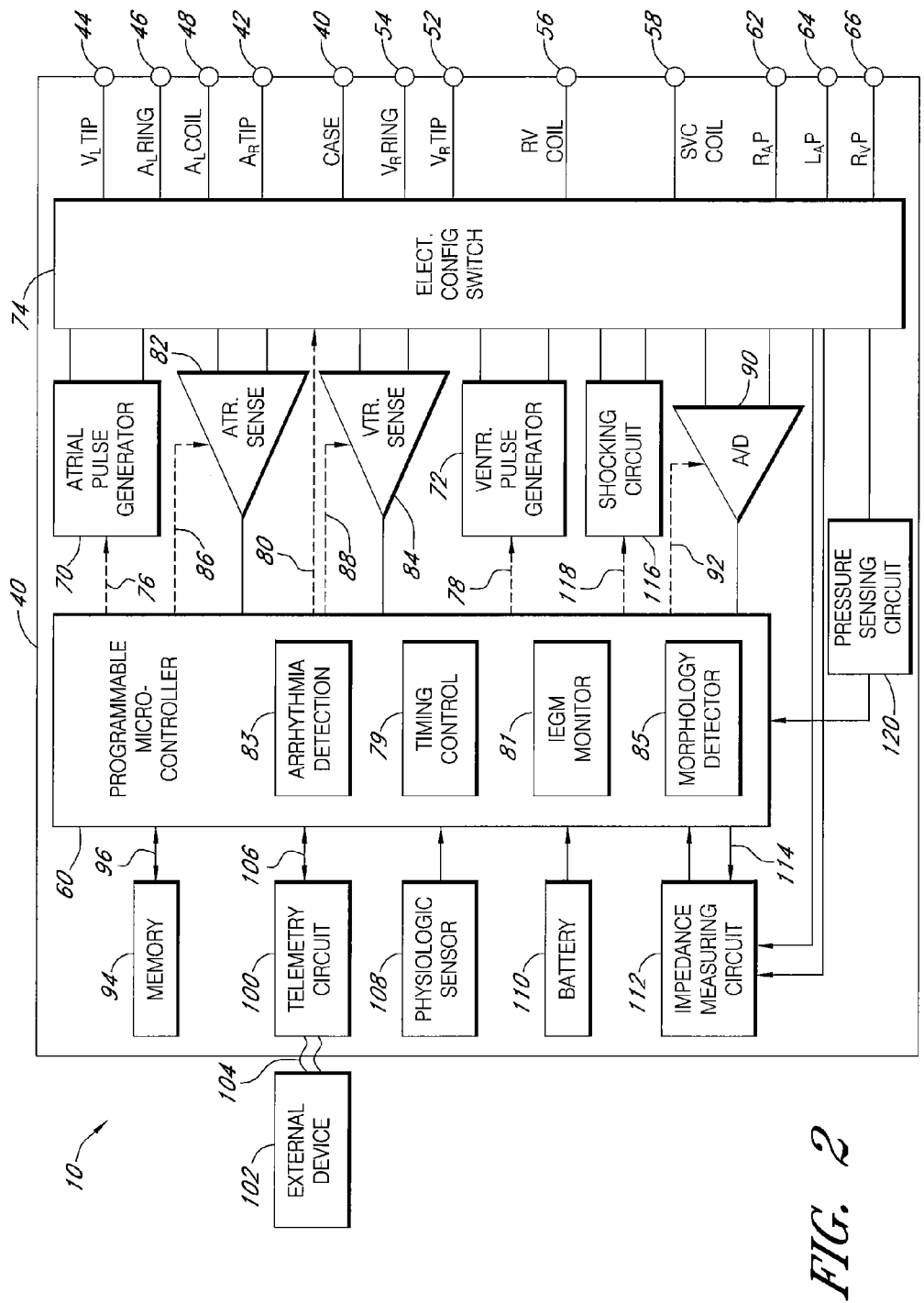
FIG. 2 is a functional block diagram of a multi-chamber implantable stimulation device of FIG. 1, illustrating the basic elements of a stimulation device which can provide cardioversion, defibrillation, and pacing stimulation, can sense cardiac activity and pressure in four chambers of the heart, and can sense orientation of a patient.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the can, case, or case electrode and may be programmably selected to act as the return electrode for all unipolar modes. The housing 40 may further be used as a return electrode alone or in combination with one or more of the coil electrodes, 28, 36, and 38, for shocking purposes. The housing 40 further includes a connector (not shown) having a plurality of terminals, 42, 44, 46, 48, 52, 54, 56, 58, 62, 64, and 66 (shown schematically and, for convenience, the names of the electrodes to which they are connected are shown next to the terminals). The connector includes at least a right atrial tip terminal ($A_R$ TIP) 42 adapted for connection to the atrial tip electrode 22 to achieve right atrial sensing and pacing.

The connector further includes at least a left ventricular tip terminal ($V_L$ TIP) 44, a left atrial ring terminal ($A_L$ RING) 46, and a left atrial shocking terminal ($A_L$ COIL) 48 to achieve left chamber sensing, pacing and shocking. The left ventricular tip terminal ($V_L$ TIP) 44, left atrial ring terminal ($A_L$ RING) 46, and left atrial shocking terminal ($A_L$ COIL) 48 are adapted for connection to the left ventricular ring electrode 26, the left atrial tip electrode 27, and the left atrial coil electrode 28, respectively.

The connector also includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58 to support right chamber sensing, pacing and shocking. The right ventricular ring terminal ($V_R$ RING) 54, right ventricular shocking terminal ($R_V$ COIL) 56, and SVC shocking terminal (SVC COIL) 58 are adapted for connection to the right ventricular tip electrode 32, right ventricular ring electrode 34, the RV coil electrode 36, and the SVC coil electrode 38, respectively.

The connector further includes at least a right atrial pressure sensing terminal ($R_AP$) 62, a left atrial pressure sensing terminal ($L_AP$) 64, and a right ventricular pressure sensing terminal ($R_VP$) 66 to achieve pressure sensing. The right atrial pressure sensing terminal ($R_AP$) 62, left atrial pressure sensing terminal ($L_AP$) 64, and right ventricular pressure sensing terminal ($R_VP$) 66 are adapted for connection to the right atrial pressure sensor 14, the left atrial pressure sensor 15, or the right ventricular pressure sensor 18.

At the core of the stimulation device 10 is a programmable microcontroller 60 which controls the various modes of stimulation therapy. As is well known in the art, the microcontroller 60 typically includes a microprocessor or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the sensing polarity of the cardiac signal by selectively closing the appropriate switches, as is also known in the art. In this way, the clinician may program the sensing polarity independent of the stimulation polarity.

Each sensing circuit, 82 and 84, preferably employs one or more low power precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical or a pressure signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Electrical cardiac signals are also applied to the inputs of an analog-to-digital (A/D) data acquisition system 90. The data acquisition system 90 is coupled to the right atrial lead 20, the coronary sinus lead 24, and the right ventricular lead 30 through the switch 74 to sample cardiac signals across any pair of desired electrodes. The data acquisition system 90 is configured to acquire IEGM signals, convert the raw analog data into digital signals, and store the digital signals for later processing, telemetric transmission to an external device 102, and/or further processing by an IEGM monitor 81.

The data acquisition system 90 may be coupled to the microcontroller 60 and the IEGM monitor 81, or other detection circuitry, for detecting an evoked response from the heart 12 in response to an applied stimulus, thereby aiding in the detection of capture. Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which are hereby incorporated herein by reference. The type of capture detection system used is not critical to the present invention.

Generally, if a capture is not detected after applying an electrical stimulus, at least one other electrical stimuli is applied to the heart immediately thereafter to prevent occurrence of cardiac arrhythmias. In some embodiments, depending on the characteristics of the cardiac signals sensed, certain parameters of the electrical stimulus that will be applied to the heart may be changed. For example, voltage may be increased to produce a more effective shock.

In addition to detecting capture, the microcontroller 60 includes the IEGM monitor 81 for receiving and monitoring the IEGM signals to detect possible abnormalities in the cardiac signals. The IEGM monitor 81 is coupled to and can receive IEGM signals from the data acquisition system 90. The IEGM monitor 81 then analyzes the IEGM signals by comparing the signals to stored parameters to detect substantial differences in amplitude, phase, wave shape, and/or other characteristics of the cardiac signal. The stored parameters are generally predetermined and may be input to the ICD by a physician or other clinician. Alternatively, the stored parameters may originate from the patient's own previously monitored cardiac activity.

The timing intervals between sensed events (e.g., P-waves, R-waves, and depolarization signals associated with fibrillation) may also be classified by the microcontroller 60 by comparing them to the predefined rate zone limit (e.g., bradycardia, normal, low rate VT, high rate VT, and fibrillation rate zones) and various other characteristics (e.g., sudden onset, stability, physiologic sensors, and morphology, etc.) to determine the type of remedial therapy that is needed (e.g., bradycardia pacing, anti-tachycardia pacing, cardioversion shocks or defibrillation shocks, collectively referred to as tiered therapy). Additionally, depending on the characteristics of the sensed signals, some parameters of electrical stimulus that will be applied to the heart may be changed. For example, in some instances, the voltage of the signal may be increased.

Differences between the waveform characteristics of the captured cardiac signal and the stored waveform parameters do not always, however, result from abnormalities and/or cardiac arrhythmias. Some differences, for example, result from the patient's physical activity or physical orientation. For example, the peak to peak amplitude of the IEGM signal may change by as much as 15% depending on the physical orientation of the patient. It is therefore advantageous for the stimulation device 10 to be able to detect abnormalities that are due to conditions other than abnormal conditions of the heart, so the device 10 does not respond improperly to these conditions.

Figure 3:
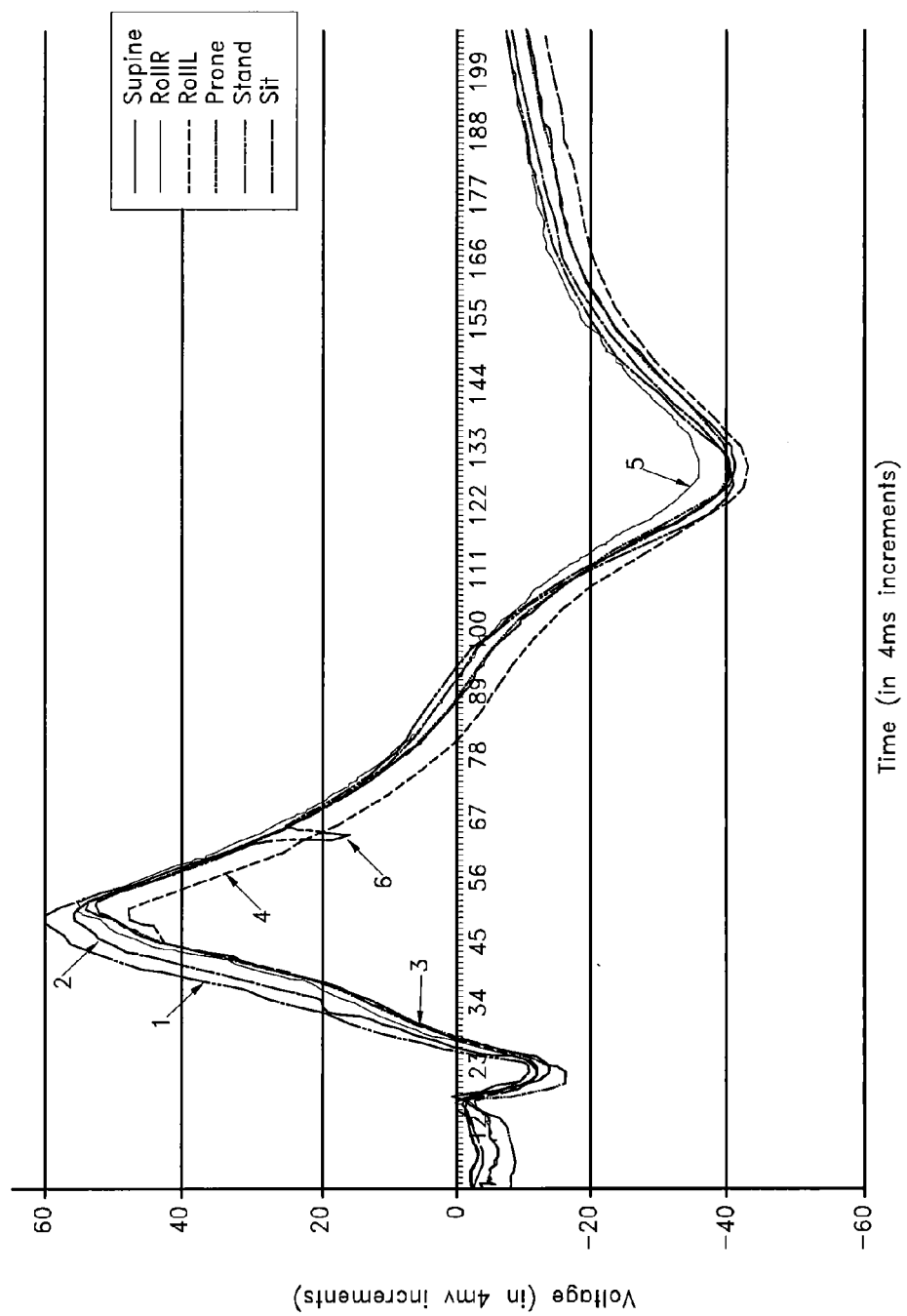
FIG. 3 is a graph of intracardiac electrogram signals obtained from a patient in different orientations.

FIG. 3 shows an exemplary IEGM graph. Signals 1-6 of FIG. 3 were obtained from the same patient when placed into standing, sitting, supine (lying on the back), rolling on the left, rolling on the right, and prone (lying on the stomach) positions, respectively. As illustrated, the amplitude of the IEGM signal can change significantly when patient orientation is changed. Additionally, other parameters of the IEGM signal, such as, timing, frequency, phase, and the like can also change as a function of patient orientation. Thus, if changes in orientation are not identified and properly considered or discounted, the stimulation device 10 may respond improperly. For example, the stimulation device 10 could improperly trigger a remedial therapy and/or change parameters of the electrical stimuli applied to the heart. Thus, in one embodiment, the physical orientation of the patient is determined and taken into account before parameters are changed.

Figure 4:
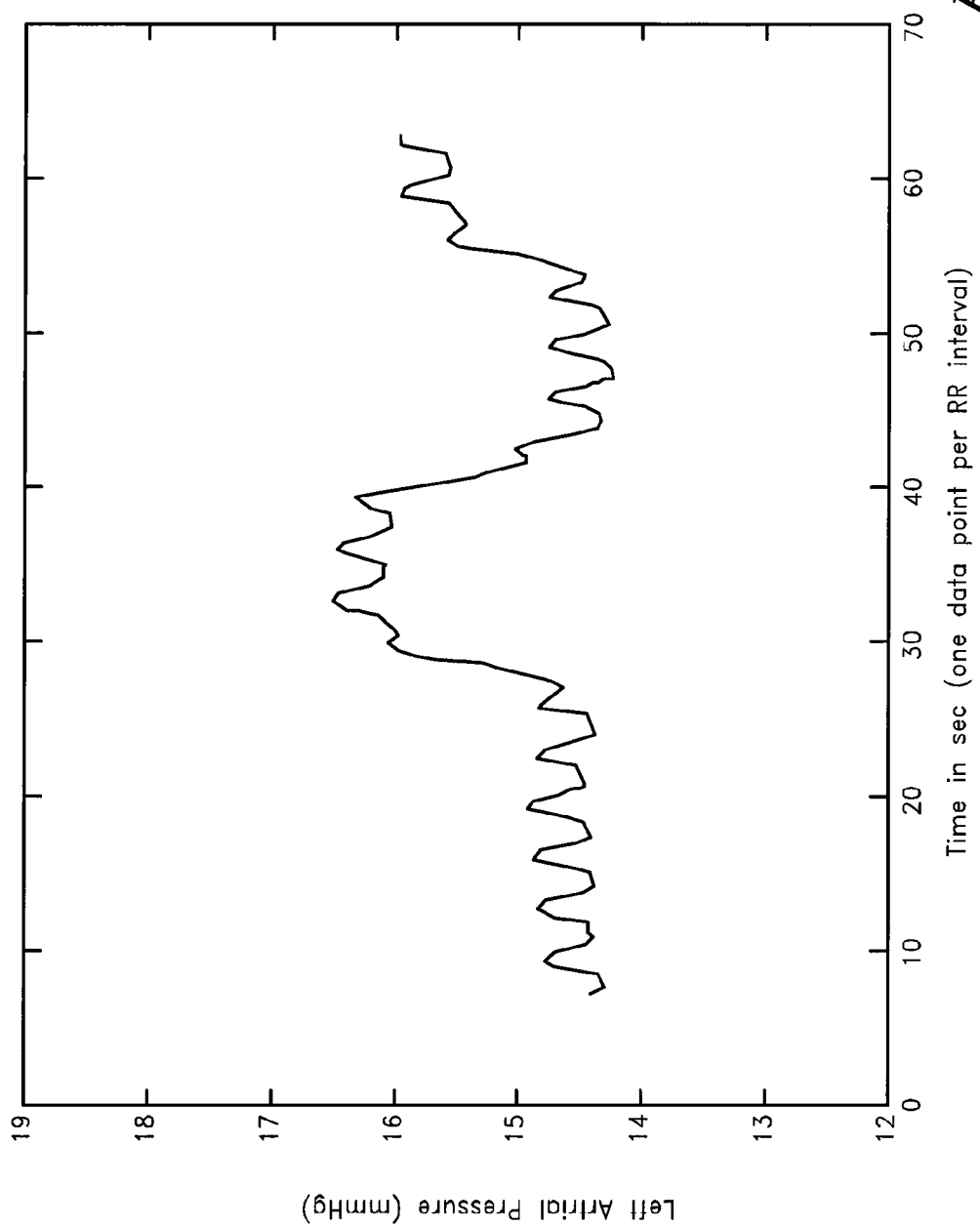
FIG. 4 is a graph a left atrial pressure signal illustrating a change in pressure when patient orientation changes.

Changes in the patient's orientation may be detected by pressure sensors. FIG. 4 illustrates one such change in the left atrial pressure of a patient with normal heart conditions. The sudden change in the amplitude of the left atrial pressure signal, shown in FIG. 4, occurred as a result of a change in the orientation of the patient from a supine position to a position where the patient's head was tilted down. Thus, pressure sensors and/or other physiological sensors can be used to detect changes in the patient's orientation.

For example, in one embodiment, the pressure monitoring circuit 120 of FIG. 2 receives and processes pressure signals sensed by the pressure sensors 14, 15, and 18. In one embodiment, the pressure sensors and their associated electronics are integrated within sensor modules attached to the distal end of the leads 20, 24, and 30. In one embodiment, the distal sensor module includes a miniature hermetically sealed housing. In one embodiment, the housing is cylindrical, with a diameter equal to or about the diameter of the leads. In one embodiment, the pressure sensor leads may also be used for pacing, with all or preferentially a portion of the outside of the sensor housings used as one of the electrodes of the pacemaker. In some configurations, some of the pacing electronics (e.g., an output pulse and input (sense) amplifier, filter, threshold detector and refractory circuit) are integrated within the sensor housing and implanted within the heart. This may be advantageous in that separate sensing and pacing electrodes can be provided at or near the distal module without requiring separate sense and pacing conductors within the lead.

Figure 5:
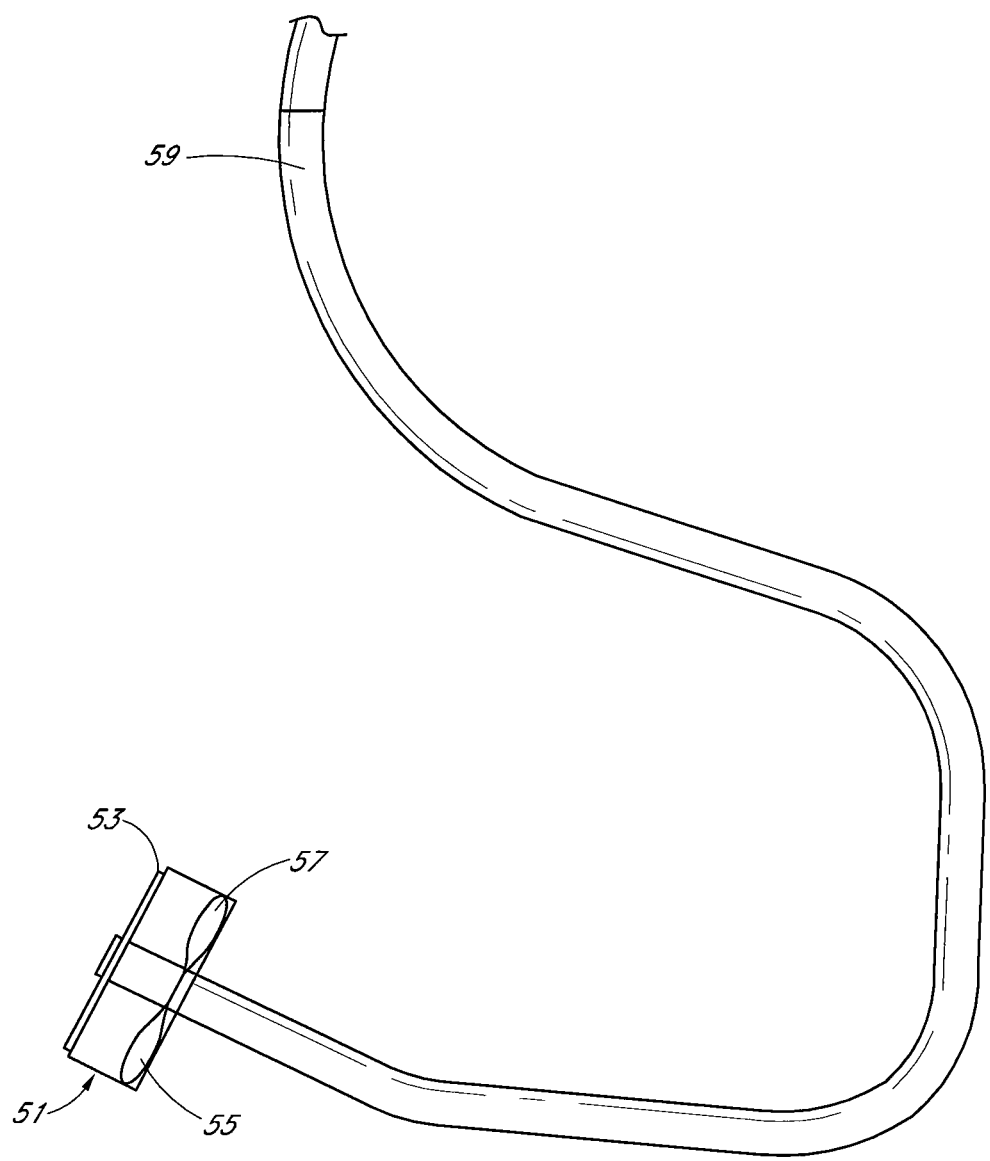
FIG. 5 is a simplified diagram illustrating an implantable stimulation device in electrical communication with at least one lead having a pressure sensor at its distal end.

FIG. 5 illustrates one embodiment of a pressure sensor and/or electrode that can be used with the stimulation device 10. The pressure sensor 51 has a distal end 53 and a proximal end 55. An anchoring mechanism 57 is located at or near the proximal end 55. The anchoring mechanism 57 is configured to anchor the sensor package 31 to the septum of a patient's heart. The pressure sensor 51 is located at or near the distal end of a lead 59. In this embodiment, the sensor package 51 includes a metallic housing, which functions and acts as an electrode for sensing IEGM signals. The lead 59 is a lead, such as, one of the leads 20, 24, and 30 of FIG. 1 and can be coupled to the stimulation device 10 at the other end.

Referring back to FIG. 1, it should be noted that although three pressure sensors 14, 15, and 18 are shown, in accordance with other embodiments of the present invention, one or two pressure sensors may be used. Thus, in some embodiments, only one pressure sensor is included. For example, in certain embodiments the device only includes a right atrial pressure sensor 14, a left atrial pressure sensor 15, or a right ventricular pressure sensor 18.

Other combinations are is also possible. For example, in some embodiments, the device includes two pressure sensors, e.g., a right atrial pressure sensor 14 and a left atrial pressure sensor 15; a right atrial pressure sensor 14 and a right ventricular pressure sensor 18; or a left atrial pressure sensor 15 and a right ventricular pressure sensor 18.

In other configurations the pressure sensors are located at locations other than those illustrated in FIG. 1. For example, in certain embodiments, a pressure sensor may be located in the atrial septum, the left atrial appendage, the left atrial free wall, one of the pulmonary veins, or any other location in pressure communication with the left atrium. For example, the pressure sensor can be located at, in, or near the right atrium, the central veins, or any location as known to those of skill in the art suitable for measuring a pressure related to the cardiac pressure. Such cardiac pressures include the pulmonary veins pressure, the pulmonary capillary wedge pressure, the pulmonary artery diastolic pressure, the left ventricular end diastolic pressure, or the right ventricular end diastolic pressure.

In one embodiment, the pressure signals include pulmonary vein pressure, pulmonary capillary wedge pressure, pulmonary artery diastolic pressure, left ventricular end diastolic pressure, right ventricular end diastolic pressure, right atrial pressure, or the pressure measured in the intrathoracic space, or the central veins. In another embodiment, the signals include algorithms that estimate pulmonary artery diastolic pressure from the right ventricular waveform, the right ventricular end diastolic pressure, the right atrial pressure, or the response of the arterial blood pressure to the Valsalva maneuver. In yet another embodiment, signals indicative of left atrial pressure include spatial parameters (e.g., dimension of chambers), septal shape, position, motion, and acceleration.

In some embodiments, the pressure sensors include pressure transducers. In one embodiment, the pressure transducers may be contained within hermetically sealed sensor packages, sometimes referred to as modules. The sensor packages may be provided in a wide range of sizes and shapes. In one embodiment, the sensor package is cylindrical, and is between about 1 mm and 5 mm long, and 3 mm in diameter. In another embodiment, the sensor package is between about 5 mm and about 15 mm long. In another embodiment the package is about 8 mm long, and about 3 mm in diameter. In one embodiment the package is less than about 1 mm in diameter. In another embodiment, the package is less than about 10 mm long.

Micro electro-mechanical system (MEMS) pressure sensor devices may also be used. In one embodiment, the package is rectangular, square, spherical, oval, elliptical, or any other shape suitable for implantation. In one embodiment, the sensor package is rigid, and in another embodiment, the sensor package may be flexible.

In one embodiment, the sensor package includes a titanium cylindrical housing that is closed at one end by titanium foil membrane. In one embodiment, the foil membrane is between about 0.001 to 0.003 inches, between about 0.003 inches and about 0.005 inches, or less than 0.001 inches thick. In another embodiment, the foil membrane is between about 0.001 inches to about 0.002 inches (about 25 microns to about 50 microns) thick, and about 0.08 to 0.10 inches (about 2.0 to 2.5 mm) in diameter. Foil diaphragms of this type have relatively low compliance, meaning that they exhibit relatively little strain, or displacement, in response to changes in pressure. For example, in one embodiment, a 2.5 mm diameter by 50-micron thick titanium foil diaphragm has a displacement at its center of only about 4.3 nanometers per mm Hg pressure change.

In one embodiment, resistive strain gauges are bonded to the inside surface of the foil.

In one embodiment, the titanium cylindrical housing includes an application specific integrated circuit (ASIC or chip) or measurement electronics. Measurement electronics are contained within the housing, connected to the strain gauges by fine gold wires. The other end of the housing may be sealed by a ceramic feed-through that is brazed to the titanium cylinder.

In one embodiment, the pressure of the gas sealed in the cylinder may be slightly lower than the lowest external pressure anticipated, so that the net force on the foil will be inward under normal conditions of operation. This will form a concave membrane shape. The advantage of maintaining a concave membrane shape throughout the pressure range of operation is that it avoids potential pressure measurement artifacts that are known to sometimes occur when a pressure sensing membrane transitions between a concave and a convex shape, a phenomenon known as oil-canning. In one embodiment, oil-canning is avoided by using a transducer diaphragm that has low compliance, as described above, and that is nearly flat in the absence of a pressure differential. In one embodiment, the diaphragm is about 2.0 to 2.5 mm in diameter and is within about 25 microns of flat in the absence of a pressure differential. In another embodiment, the diaphragm thickness is maximized to maximize flatness and minimize compliance.

Referring back to FIG. 2, the microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

One feature of the present invention is the ability to sense and store a relatively large amount of data (e.g., from the data acquisition system 90), which data may then be used for subsequent analysis to guide the programming of the device and/or diagnose potential heart problems. For example, data relating to any abnormalities detected in the IEGM signals may be stored for future analysis. Such data may be useful in early detection of heart failures or other potential heart problems. To conserve memory and power and to prevent an improper diagnosis, however, abnormalities that are due to external factors, such as orientation of the patient need to be eliminated. Thus, it is advantageous to take into account the orientation of the patient before storing data relating to an abnormality in the amplitude of the IEGM signals.

In one embodiment, the stimulation device 10 further includes a physiologic sensor 108. The physiologic sensor 108 may be used to detect changes in the cardiac output, changes in the physiological condition of the heart, or changes in the orientation of the patient. In response to changes detected by the physiologic sensor 108, the microcontroller 60 may adjust various pacing parameters (such as rate, AV Delay, V-V Delay, etc.) at which the atrial and ventricular pulse generators, 70 and 72, generate stimulation pulses. In one embodiment, the physiologic sensor 108 is an orientation sensor such as an accelerometer which, as illustrated in FIG. 2, is located within the housing 40 of the stimulation device 10.

The orientation sensor 108 detects both static positional orientation and changes in the orientation of the patient. While shown as being included within the stimulation device 10, the orientation sensor 108 can also be external to the stimulation device 10, yet still be implanted within or carried by the patient. For example, the orientation sensor 108 may be placed on a lead or implanted in the patient's heart.

In one embodiment, the orientation sensor 108 is a 3 dimensional (3D) accelerometer. In another embodiment, the orientation sensor 108 includes a plurality of accelerometers that are arranged in an orthogonal shape. The accelerometer 108 obtains an analog signal which represents the patient's movement and/or the patient's static orientation. Thus, the accelerometer is capable of detecting both dynamic and static positional orientations. This is different from 1 dimensional (1D) accelerometers in that 1D accelerometers sometimes can not detect static positional orientations. The accelerometer 108 converts the analog signal to a digital signal which identifies the movement or the static orientation of the patient. Alternatively, the analog to digital conversion can be done by other circuit components, such as the data acquisition 90. For example, the accelerometer 108 can detect whether the patient is in a face down supine position, a seated/standing position, lying to the right, or lying to the left.

In another embodiment, one or more pressure sensors may be used in combination with the accelerometer 108 to determine patient orientation. For example, pressure sensors may be used in combination with the accelerometer 108 to determine whether the patient is in a standing or in a seated position.

Thus, the accelerometer 108 when used in combination with the pressure sensors 14, 15, and/or 18 can detect various movements and/or static positional orientations of a patient. This is advantageous in diagnosis and treatment of various abnormalities. For example, patients suffering from orthostatic hypotension may benefit from this, because the device can detect when they stand up and can increase the pacing rate to compensate for their hypotension.

In certain embodiments, the accelerometer 108 is often the type described in U.S. Pat. Nos. 5,383,473 and 5,593,431, the entire disclosure of which are hereby incorporated by reference. In addition to the accelerometer 108, the microcontroller 60 includes a morphology detector 85 for detecting morphology and analyzing the IEGM signals. The morphology detector 85 can work as a pattern recognition algorithm, as known in the art, which recognizes patterns based on known feature matching techniques.

The stimulation device 10 further includes a battery 110 which provides operating power to all of the circuits shown in FIG. 2. For the stimulation device 10, which employs shocking therapy, the battery 110 is generally capable of operating at low current drains for long periods of time, and capable of providing high-current pulses (for capacitor charging) when the patient requires a shock pulse. The battery 110 also generally has a predictable discharge characteristic so that elective replacement time can be detected. In one embodiment, the device 10 preferably employs a lithium/silver vanadium oxide battery.

As further shown in FIG. 2, the device 10 also has an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it generally detects the occurrence of an arrhythmia, and automatically applies an appropriate electrical shock therapy to the heart aimed at terminating the detected arrhythmia. Thus, the microcontroller 60 further includes an arrhythmia detection circuit 83 for detecting arrhythmias. Furthermore, the microcontroller 60 controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 6A:
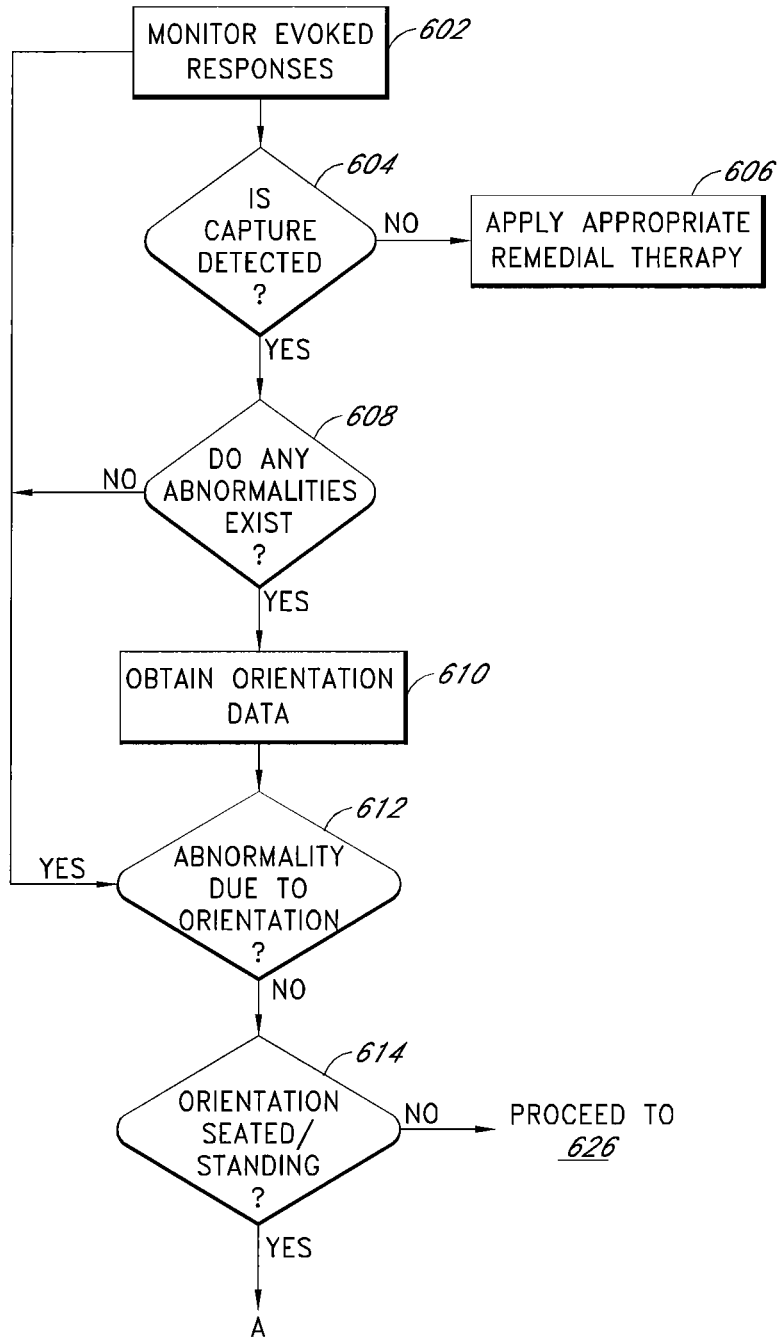
FIGS. 6A and 6B are flow-charts of one embodiment of a method of detecting an orientation of a patient using an orientation sensor and at least one pressure sensor.
Figure 6B:
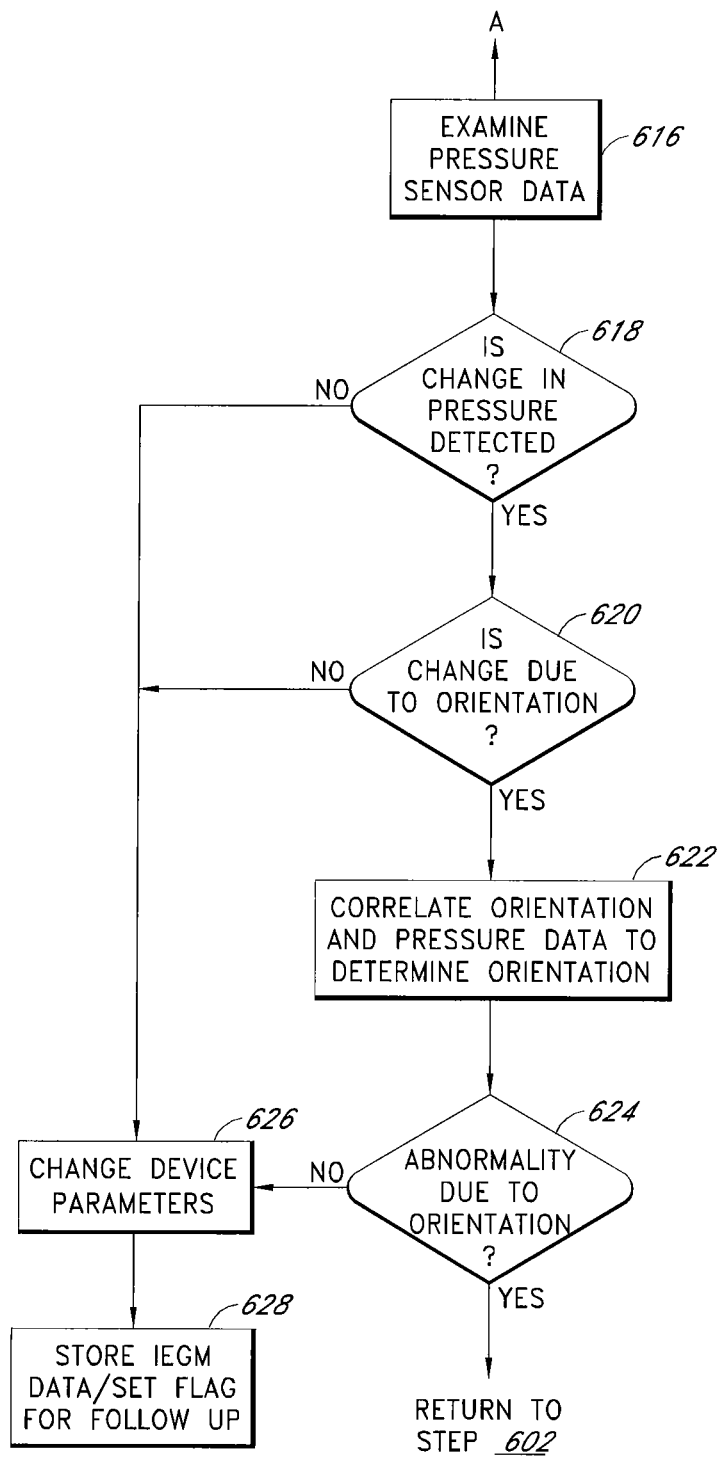

FIGS. 6A and 6B illustrate a flow chart of one embodiment of a method 600 describing an overview of the operation and novel features implemented in the device 10. In this flow chart and the other flow charts described herein, the various algorithmic steps are summarized in individual blocks. Such blocks describe specific actions or decisions that must be made or carried out as the algorithm proceeds. Where a microcontroller (or equivalent) is employed, the flow charts presented herein provide the basis for a control program that may be used by such a microcontroller (or equivalent) to effectuate the desired control of the stimulation device. Those skilled in the art may readily write such a control program based on the flow charts and other descriptions presented herein. It will be understood that the steps, processes, and components of the method 600 would generally proceed in parallel with the other operations and processes of the device 10 as previously described.

The method 600 begins in a step 602 where evoked responses are monitored. This can be achieved by sensing the cardiac activity each time an electrical stimulus is applied to the heart. In one embodiment, a data acquisition system is configured to receive analog cardiac signals, convert the analog signals to digital signals, and provide them to an IEGM monitor where the signals are further analyzed.

In step 604, the method 600 determines whether a capture has occurred. If the method 600 detects that a capture has not occurred, the method 600 proceeds to step 606 where an appropriate remedial therapy is applied to the heart. If a capture is detected, then the method 600 proceeds to step 608 to determine if any abnormalities exist in the detected IEGM signals.

Abnormality detection can be achieved by comparing the characteristics of the detected cardiac signals at step 604 to predetermined parameters and determining if there are notable differences between any of the characteristics and their corresponding predetermined parameters. In one embodiment, the predetermined parameters are stored in a memory of a cardiac stimulation device. If any differences are detected between the sensed characteristics and their corresponding predetermined parameters and the differences exceed predetermined thresholds, then the differences are marked as irregularities.

However, as discussed above, changes in the IEGM signals may result from a variety of factors that may not be related to abnormalities of the patient's heart. Thus, in one embodiment, before responding to the abnormality by, for example, changing the parameters of the cardiac stimulation device or storing the abnormality in memory for later analysis, other factors that may have contributed to the difference are detected. One such factor is the orientation of the patient, because the amplitude of the IEGM signal may change by as much as 15%, depending on the orientation of the patient. Thus, according to one embodiment, the method determines whether the abnormality is due to the orientation of the patient before responding to a detected abnormality.

Accordingly, in step 610, the method 600 obtains data relating to the orientation of the patient from an orientation sensor, such as a 3D accelerometer. In step 612, the method 600 determines whether the abnormality is due to the orientation of the patient. This may be achieved by correlating the detected abnormality with data stored in memory that corresponds to the detected orientation to determine whether the difference is due to the patient's orientation.

For example, if the detected abnormality is a 10% increase in the amplitude of the IEGM signal, and the orientation sensor detects that the patient is in a seated position, normal amplitude values for a seating position stored in memory may be looked up to determine whether the detected amplitude value is notably different from the normal value. If the detected amplitude falls within the range of normal values, then the method 600 decides that the abnormality is due to the orientation of the patient.

If the method 600 determines that the abnormality is due to the orientation of the patient, then the method 600 returns to step 602 to continue monitoring the evoked responses. If the method 600 determines that the detected abnormality is not due to the orientation, then the method 600 proceeds to step 614 to determine if the detected orientation is a seated or standing position. This is done to assure that the orientation is detected correctly. Since the positional vectors for the seated and standing positions are sometimes the same, an accelerometer may not be able to detect between these two positions. Thus, if the detected position is one of these orientations, then other sensors, such as, one or more pressure sensors may be used in combination with the accelerometer to assure that the correct position has been detected. Accordingly, if it is determined in step 614 that the detected orientation is a seated or standing position, then the method 600 proceeds to a step 616 of FIG. 6B to determine the correct orientation. However, if at step 614 the detected position is not one of standing or seated, then the method 600 proceeds to a step 628, as described below.

In step 616, data from one or more pressure sensors, for example, any one of the pressure sensors described herein, is examined. Pressure sensor data are continually obtained by a pressure sensing circuit and are examined in step 616 by a microcontroller to detect a change in pressure. If a change in pressure is detected in step 618, then the method 600 proceeds to step 620, to determine whether the change in pressure is due to a change in the patient's orientation.

If the method 600 determines in step 620 that the change in pressure is not related to a change in the patient's orientation, then the method 600 proceeds to step 628, described below. However, if the method 600 determines in step 620 that the change in pressure is due to a change in orientation, then data from the accelerometer is correlated with the data from the pressure sensors to determine the patient orientation in step 622. This may be achieved, for example, by first examining the change in pressure and comparing the values to predetermined values to determine what change of orientation the change in pressure may correspond to. This information, then, may be compared against accelerometer data to confirm that the detected orientation is correct.

After detecting the patient's orientation, the method 600 proceeds to step 624, where it correlates the detected abnormality with the patient orientation to determine whether the abnormality is due to the patient's orientation. This is achieved using the methods described previously herein. If the abnormality is due to the orientation, then in step 626, the method 600 returns to step 602 of FIG. 6A to continue monitoring the evoked response. However, if it is determined that the abnormality is not due to patient orientation, as determined in step 624, then the method 600 proceeds to step 628.

At step 628, the method 600 determines whether any device parameters should be changed in response to the abnormality and changes those parameters accordingly. Then, the method 600 proceeds to step 630 to store the IEGM data corresponding to the abnormality in memory and set a flag in memory for later follow up of a physician or health care provider. Thus, the next time a physician or health care provider examines the device, he/she can review and analyze the abnormality. This may aid in early diagnosis of potential heart failures and/or other problems and is advantageous in that it enables patients to take preventive measures.

Figure 7:
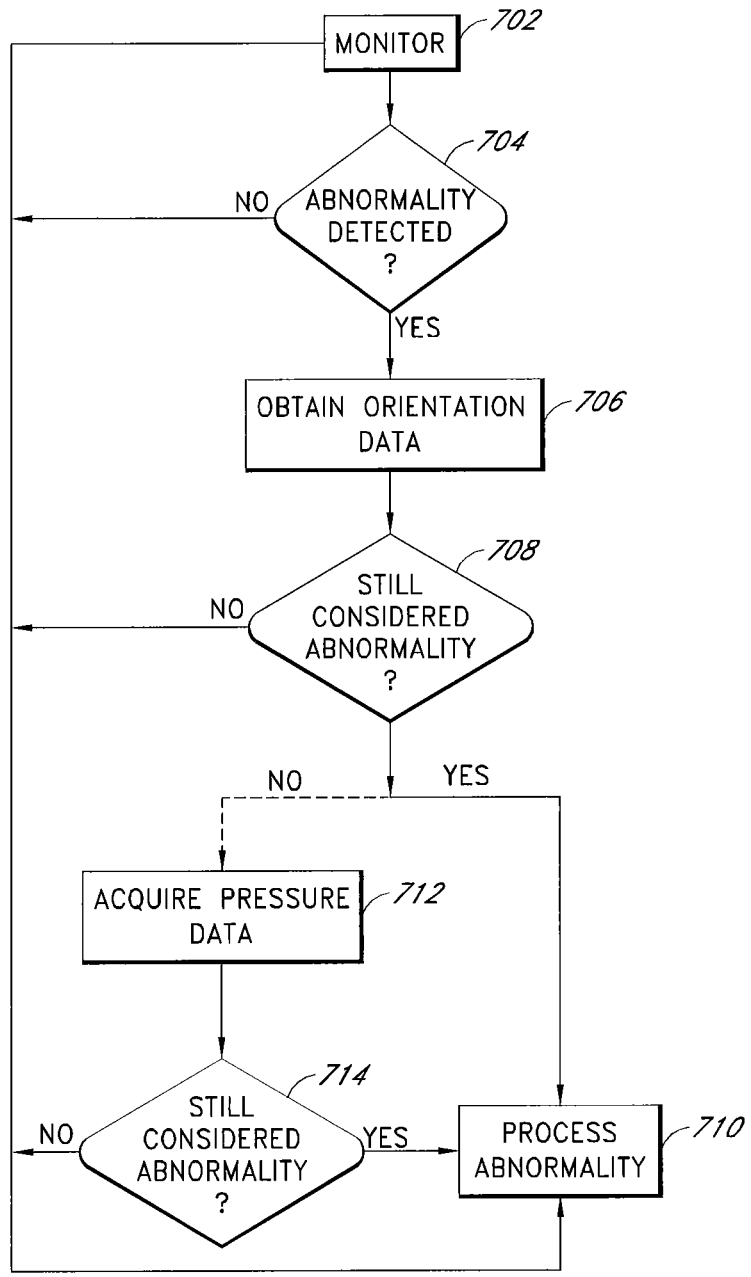
FIG. 7 is a flow-chart of one embodiment of a method of detecting an orientation of a patient using an orientation sensor.

The method 600 is one embodiment of a method to detect patient orientation and other methods are also possible. For example, FIG. 7 illustrates a flow chart of one embodiment of a method 700 describing an overview of the operation and novel features implemented in the device 10.

The method 700 begins in a step 702 where evoked responses are monitored, as described previously. The method 700 proceeds to step 704 to determine if any abnormalities exist in the detected IEGM signals. This may be achieved by methods and systems described previously herein. If the method 700 determines that there are no abnormalities, then the method returns to step 702 to continue monitoring the evoked response. However, if the method 700 determines that there is an abnormality, then the method 700 proceeds to step 704 to obtain a patient orientation. The patient orientation may be obtained by an orientation sensor such as an accelerometer described herein. After obtaining the patient orientation, the method 700 proceeds to step 706 to determine whether the abnormality is due to the patient's orientation.

If the method 700 determines that the abnormality is due to the patient's orientation and should thus not be considered an abnormality, then the method 700 returns to step 702 to continue monitoring the evoked response. If, however, the method 700 determines that the abnormality is not due to patient orientation, then the method 700 proceeds to step 708 to process the abnormality. The method 700 may process the abnormality in a variety of different ways in step 708. For example, in one embodiment, the method 700 flags the detected IEGM signal as abnormal and stores the data in a memory. In another embodiment, the method 700 changes the parameters of a cardiac stimulation device.

In one embodiment, after determining at step 706, that the abnormality is not due to the patient orientation, the method 700 proceeds to step 710 where it acquires data from one or more pressure sensors. The data from the one or more pressure sensors is examined at step 712 to determine whether the pressure data confirms that the abnormality is not due to the patient orientation. If the method 700 determines that the pressure data shows the abnormality is in fact due to patient orientation, then the method 700 returns to step 702 to continue monitoring the evoked responses. If, however, the method 700 determines that the pressure data confirms the abnormality is not due to patient orientation, then the method 700 proceeds to step 708 to process the abnormality, as discussed previously.

In one embodiment, care is taken to maintain the values of parameters of the stimulation pulses (e.g., pacing rate, pacing pulse width, pacing amplitude and the like) applied to the heart constant. This is done because changes in the parameters of the stimulation pulses can also result in changes in the detected IEGM signals. Thus, in another embodiment, parameters of each stimulation pulse applied to the heart are stored in memory. In this embodiment, when abnormalities are detected in the IEGM signals, the method determines if parameters of the last stimulation pulse applied to the heart are different from parameters of the stimulation pulse applied to the heart before the last stimulation pulse. If the parameters are different, the method determines that the abnormality is due to the change in parameters and thus continues monitoring the evoked responses.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation system for a patient comprising:
   at least one lead adapted to be implanted within the patient so as to be able to provide electrical stimulation to the heart of the patient;
   at least one electrical sensor that senses internal electrogram signals which include signals indicative of intrinsic heart activity and evoked heart activity in response to the delivery of therapeutic electrical stimulations via the at least one lead;
   a pressure sensor that senses a pressure within at least one chamber of the heart;
   an orientation sensor that detects parameters of the patient that are indicative of an orientation of the patient, wherein the orientation sensor comprises at least one accelerometer and wherein the orientation of the patient is determined using both the pressure sensor and the accelerometer;
   a controller that induces the cardiac system to deliver electrical stimulation to the heart of the patient via the at least one lead wherein the controller receives internal electrogram signals from the at least one electrical sensor and signals from the orientation sensor, wherein the controller evaluates the internal electrogram signals from the at least one electrical sensor to determine whether the internal electrogram signals are potentially indicative of possible abnormality in the patient's heart function and when the controller determines that the internal electrogram signals are potentially indicative of possible abnormalities in the patient's heart function, the controller then evaluates the orientation sensor to determine whether the possible abnormalities are due, at least in part, to a change in the orientation of the patient.

2. The device of claim 1, wherein the controller is adapted to evaluate whether the possible abnormalities are due to a change in the orientation of the patient and the controller is configured to store the internal electrogram signals relating to the possible abnormality in a memory and set a flag in the memory for future follow up, when the controller determines that the possible abnormalities are not due to a change in the patient's orientation.

3. The device of claim 1, wherein the controller is adapted to evaluate whether the possible abnormalities are due to a change in the orientation of the patient and the controller is configured to change the parameters of the electrical stimulation applied to the heart, when the controller determines that the possible abnormalities are not due to a change in the patient's orientation.

4. The device of claim 1, wherein the at least one lead is adapted to both provide electrical stimulation and also detect electrical activity of the heart so that the at least one lead comprises the at least one electrical sensor.

5. The device of claim 1, wherein an amplitude of internal electrogram signal changes as a result of a change in the patient's orientation.

6. The device of claim 5, wherein the controller monitors the evoked heart activity to determine whether the evoked heart activity has amplitude that is less than a pre-determined threshold and when the amplitude is less than a pre-determined threshold, the controller determines the signals to be potentially indicative of possible abnormalities.

7. The device of claim 6, wherein the controller then determines using the orientation sensor whether the possible abnormality is an artifact of the patient's orientation.

8. The device of claim 1, wherein the accelerometer is positioned inside the implantable cardiac stimulation device.

9. The device of claim 1, wherein the accelerometer is configured to detect the patient's static positional orientation.

10. The device of claim 1, wherein the accelerometer is configured to detect the patient's movement.

11. An implantable cardiac stimulation device for a patient comprising:
    at least one lead adapted to be implanted within the patient so as to be able to provide electrical stimulation to the heart of the patient;
    at least one electrical sensor that senses internal electrogram signals which include signals indicative of intrinsic heart activity and evoked heart activity in response to the delivery of therapeutic electrical stimulations via the at least one lead;
    a pressure sensor that senses a pressure within at least one chamber of the heart;
    an orientation sensor that detects parameters of the patient that are indicative of the orientation of the patient; and
    a controller that induces the at least one lead to provide electrical stimulation to the heart of the patient wherein the controller receives internal electrogram signals from the at least one electrical sensor and signals from the orientation sensor, and the pressure sensor and wherein the controller evaluates the internal electrogram signals from the at least one electrical sensor to determine whether the internal electrogram signals are potentially indicative of possible abnormality in the patient's heart function and when the controller determines that the internal electrogram signals are potentially indicative of possible abnormalities in the patient's heart function, the controller then evaluates signals received from the pressure sensor and the orientation sensor to determine whether the possible abnormalities are due, at least in part, to a change in the orientation of the patient and uses the signals to adjust the electrical stimulation therapy being provided to the heart via the at least one lead.

12. The device of claim 11, wherein the orientation sensor comprises an accelerometer.

13. The device of claim 12, wherein the orientation sensor comprises a plurality of accelerometer arranged in an orthogonal shape.

14. The device of claim 11, wherein the at least one lead is adapted to both provide electrical stimulation and also detect electrical activity of the heart so that the at least one lead comprises the at least one electrical sensor.

15. The device of claim 11, wherein the controller evaluates the signals received from the pressure sensor and the orientation sensor to detect if the patient has stood up and evaluates the signals received from the pressure sensor to detect whether the patient suffers from orthostatic hypotension.

\* \* \* \* \*